(12) United States Patent
Amelse (10) Patent No.: US 7,405,340 B2
(45) Date of Patent: Jul. 29, 2008

(54) PROCESS FOR RECOVERING PARAXYLENE UTILIZING AMMONIA ABSORPTION REFRIGERATION

(75) Inventor: Jeffrey A. Amelse, Batavia, IL (US)

(73) Assignee: BP Corporation North America Inc., Warrenville, IL (US)

( * ) Notice: Subject to any disclaimer, the term of this patent is extended or adjusted under 35 U.S.C. 154(b) by 634 days.

(21) Appl. No.: 10/816,318

(22) Filed: Apr. 1, 2004

(65) Prior Publication Data

US 2005/0228206 A1    Oct. 13, 2005

(51) Int. Cl.
*C07C 7/14* (2006.01)
(52) U.S. Cl. .................................................... 585/812
(58) Field of Classification Search ............... 203/48; 585/805, 812, 815
See application file for complete search history.

(56) References Cited

U.S. PATENT DOCUMENTS

| | | | | |
|---|---|---|---|---|
| 2,809,815 | A | * 10/1957 | Born | 366/310 |
| 3,067,270 | A | * 12/1962 | Weedman | 203/48 |
| 3,177,265 | A | 4/1965 | Lammers | 260/674 |
| 3,541,804 | A | 11/1970 | Wiegandt et al. | 62/58 |
| 3,662,562 | A | 5/1972 | Wiegandt et al. | 62/123 |
| 3,722,229 | A | 3/1973 | Kayahara et al. | 62/354 |
| 4,116,652 | A | 9/1978 | Zondek | 62/534 |
| 4,331,826 | A | 5/1982 | Kagawa | 585/812 |
| 5,448,005 | A | 9/1995 | Eccli et al. | 585/812 |
| 5,811,629 | A | * 9/1998 | Hubbell et al. | 585/815 |

FOREIGN PATENT DOCUMENTS

GB    1159670    7/1969

OTHER PUBLICATIONS

H. Singh and F. Castillo, Process Life Cycle Solutions for the Case of Automated Heat Exchanger Network Retrofit, 22 App. Therm. Eng. 949-958 (2002).*
R.L. Shilling et al., Heat-Transfer Equipment in Perry's Chemical Engineers' Handbook, 7th ed. New York, McGraw-Hill, 1997, pp. 11-32-11-33.*
"Scraped Surface Heat Exchangers," SPX Process Equipment Co. (2006), available at http://www.spxprocessequipment.com/sites/wcb/products/heatex/PDF/pe-1530_votsshe_wcb.pdf.*
Bulgan, A.T., "Use of Low Temperature Energy Sources in Aqua-Ammonia Absorption Refrigeration Systems," Energy Conversion and Management, vol. 38, No. 14, pp. 1431-1438, Sep. 1997.
Fernandez-Seara et al., "Simultaneous Heat and Mass Transfer of a Packed Distillation Column for Ammonia-Water Absorption Refrigeration Systems," International Journal of Thermal Sciences, vol. 41, No. 10, pp. 927-935, Oct. 2002.
Bulgan, A.T., "Optimization of the Thermo-Dynamic Model of Aqua-Ammonia Absorption Refrigeration Systems," Energy Conversion and Management, vol. 36, No. 2, pp. 135-143, Feb. 1995.
Berlitz, T. et al., "An Ammonia-Water Absorption Refrigerator with a Large Temperature Lift for Combined Heating and Cooling," International Journal of Refrigeration, vol. 21, No. 3, pp. 219-229, May 1998.

* cited by examiner

*Primary Examiner*—Glenn Caldarola
*Assistant Examiner*—Randy Boyer
(74) *Attorney, Agent, or Firm*—Thomas A. Yassen (57) ABSTRACT

A process for recovering paraxylene from a substantially hydrocarbon feedstock. The recovery comprises cooling the hydrocarbon feedstock in at least one refrigerated crystallization stage that is indirectly refrigerated by evaporating at least a portion of a substantially liquid stream comprising ammonia. The crystallization stage may also be cooled by an ethylene refrigerant, which has been cooled by heat exchange with a substantially liquid stream comprising ammonia. The process further comprises a series of cooling substeps. This invention is also directed to an ammonia absorption refrigeration process powered by an enthalpy source from or near a paraxylene recovery unit.

13 Claims, 6 Drawing Sheets

Figure 1
Isolating Mixed Xylenes From Reformate

Figure 2
Generic Xylene Isomerization Process

Figure 3
Three Stage pX Crystallization Section

Figure 4
Three-Stage Crystallization Ethylene Refrigeration Loop

Figure 5
Crystallization Section for Recovering pX From STDP Xylenes

Figure 6
Single Stage AAR Process

PROCESS FOR RECOVERING PARAXYLENE UTILIZING AMMONIA ABSORPTION REFRIGERATION

BACKGROUND OF THE INVENTION

Paraxylene is a commodity chemical that is oxidized to terephthalic acid and purified to produce purified terephthalic acid, an intermediate in the manufacture of polyester. In 2001, the total world installed capacity of paraxylene was approximately 21 MMTA (million metric tons per annum), and 4.3 MMTA in the U.S.

The production of paraxylene begins with a suitable substantially hydrocarbon feedstock. As used herein, such a substantially hydrocarbon feedstock suitable for the production of paraxylene can come from several sources, and can be categorized into high and low paraxylene concentrations. The term "substantially hydrocarbon feedstock" refers to a hydrocarbon feedstock that comprises and often consists essentially of ethylbenzene, paraxylene, metaxylene, orthoxylene, and optionally aromatic and aliphatic hydrocarbon impurities.

Most feedstocks from which paraxylene is recovered are derived from catalytic reforming processes found in many petroleum refineries. The reformate product generally comprises $C_6$ to $C_{11}$ aromatics wherein the $C_8$ aromatics fraction generally comprise metaxylene, orthoxylene, paraxylene and ethylbenzene. Other byproducts of the reforming reaction are hydrogen, light gas, paraffins, naphthenes and heavy $C_{12}$+ aromatics. Paraxylene-containing feedstocks may also include pyrolysis gasoline, conventional toluene disproportionation products, conventional transalkylation products, and the intra-stage products of paraxylene recovery processes.

In all of these feedstocks, the xylene isomers are generally near their equilibrium distribution, which is about 25% paraxylene, about 50% metaxylene, and about 25% orthoxylene. The $C_8$ distillation fraction of these feedstocks generally comprises all of the $C_8$ aromatic isomers due to the close proximity of their boiling points. The low equilibrium concentration of paraxylene is further diluted by the presence of ethylbenzene, such that the $C_8$ fraction derived by distillation from reformate (reformate xylenes) typically comprises from about 10 to about 20 weight percent ethylbenzene, and more typically from about 15 to about 18 weight percent ethylbenzene. The $C_8$ fraction of pyrolysis gasoline typically comprises as much as about 30 to about 60 weight percent ethylbenzene, whereas the $C_8$ fraction of conventional toluene disproportionation typically comprises only about 2 to about 7 wt % ethylbenzene. Dilution by ethylbenzene and the equilibrium distribution of the xylene isomers reduces the paraxylene content of these feedstocks to as low as about 10 to about 25 weight percent paraxylene, with reformate xylenes typically comprising about 15 to about 20 weight percent paraxylene. It is understood that these feedstocks may be preprocessed to selectively remove metaxylene or orthoxylene, which would increase the paraxylene concentration. Thus, substantially hydrocarbon feedstocks with low paraxylene concentrations generally comprise less than about 50 weight percent paraxylene, commonly less than about 30 weight percent paraxylene, and from time to time less than about 20 weight percent paraxylene.

Substantially hydrocarbon feedstocks with high paraxylene concentrations generally comprise at least about 50 weight percent paraxylene, commonly at least about 70 weight percent paraxylene, and from time to time at least about 80 weight percent paraxylene. Substantially hydrocarbon feedstocks with high paraxylene concentrations arise from sources including feedstocks produced by Selective Toluene Disproportionation (STDP), selective alkylation, or selective transalkylation, as described in U.S. Pat. No. 4,097,543 and U.S. Pat. No. 4,117,026, and in W. W. Kaeding, et al., J. Catal., 67, 159 (1981). They are also found in the second or subsequent stages of multi-stage crystallization processes for recovering paraxylene from substantially hydrocarbon feedstocks with low paraxylene concentration. Substantially hydrocarbon feedstocks with high paraxylene concentration also include the paraxylene-enriched stream produced in the selective adsorption zone of a hybrid adsorption/crystallization paraxylene process, such as that described in U.S. Pat. No. 5,329,060.

Two processes useful for recovering paraxylene are low temperature crystallization, and selective adsorption on a molecular sieve. "Parex" is the most widely applied molecular sieve adsorption process, as described in D. P. Thornton, Hydrocarbon Proc. 49 (1970) at pp. 151-155, which is incorporated herein by reference. This process is based on the principle of continuous selective adsorption in the liquid phase employing fixed beds of solid adsorbent. The adsorbent is made from a zeolite, and the separation technique is based on small differences in affinity to the adsorbent. Paraxylene has the strongest affinity to the adsorbent and is thus preferentially adsorbed. The affinity of the desorbent liquid is positioned between those of paraxylene and the other feed components. When the desorbent affinity is too low, it will take a lot of effort to remove the paraxylene from the adsorbent. If the affinity is too high, the paraxylene is not capable of displacing the desorbent from the adsorbent. Furthermore, the volatility of the desorbent should differ sufficiently from that of the feed compounds to allow for separation of the paraxylene-desorbent and non-paraxylene-desorbent mixtures by distillation.

A crystallization process can also be used to recover paraxylene from a substantially hydrocarbon feedstock. Such a paraxylene crystallization process comprises an isomerization section, a fractionation section, and a crystallization section. Alternatively, such a crystallization process comprises a section for producing a substantially hydrocarbon feedstock with high paraxylene concentration, a fractionation section, and a crystallization section.

To efficiently recover a purified paraxylene from such substantially hydrocarbon feedstocks, the crystallization process includes one or more crystallization stages which generally comprise, jacketed crystallizers, which are typically scraped wall vessels with refrigerated jackets through which a vaporizing refrigerant passes. The crystallization stages may also comprise at least one reslurry drum. The crystallization stage may also comprise a scraped wall heat exchanger, where the material being crystallized is passed through a scraped tube side of the heat exchanger and vaporizing refrigerant is passed through the shell side of the heat exchanger.

Ethylene is often used as a refrigerant to recover paraxylene in paraxylene crystallization processes that use a substantially hydrocarbon feedstock, since efficient paraxylene recovery from these dilute paraxylene streams requires temperatures as low as about −90° F. Ethylene vapor generated from ethylene liquid in the crystallization stages from heat transfer from the material being crystallized exhibits a vapor pressure that is still above atmospheric pressure at these low temperatures, and thus can be conveniently used in a typical vapor recompression refrigeration loop. When using a hydrocarbon refrigerant such as ethylene, it is desirable that the refrigerant vapor pressure is above atmospheric at the temperatures encountered in the crystallization section to prevent oxygen ingress from potential leaks, which could lead to explosive mixtures.

However, since the critical temperature of ethylene is about 49° F., it is generally not possible or practical to condense ethylene in heat exchangers via air or water cooling. Thus, the ethylene vapor exiting the crystallizers is compressed and condensed by exchange with another refrigerant, typically propane or propylene. The propane or propylene circulates in another vapor recompression loop, and the propane or propylene vapor is condensed by air or water cooled exchangers. Thus, a typical practice of a paraxylene crystallization process uses this cascaded ethylene/propane or ethylene/propylene refrigeration circuit.

U.S. Pat. No. 3,177,265 issued to Lammers discloses a multi-stage crystallization process for recovering paraxylene from a $C_8$ or mixed xylene feed, wherein ethylene refrigerant is used to cool the first stage, and propane is used to cool a subsequent stage. Commercial variations of the Lammers process also utilize propane refrigerant for condensing and optionally desuperheating the ethylene refrigerant for other miscellaneous refrigeration requirements such as trim cooling of the feed to the crystallizers, and cooling of the fractionation system off-gas to improve recovery of benzene into the light aromatics byproduct stream.

U.S. Pat. No. 5,448,005 issued to Eccli et al. discloses a crystallization process for paraxylene recovery where a single temperature crystallization production stage is used for producing paraxylene from a feed having an above equilibrium paraxylene concentration, such as from a selective toluene disproportionation process. The process uses a refrigeration system to provide cooling to a temperature of about −20° F., and propane or propylene can be used for the refrigerant.

The above processes utilize propane or propylene vapor compression refrigeration loops for the recovery of paraxylene. In these loops, the propane or propylene vapors produced by the transfer of heat are subsequently compressed to a higher pressure after which the vapors can be condensed by air or water cooled heat exchangers. The propane or propylene refrigeration compressors are costly, complex and inefficient machines requiring a substantial amount of energy to operate. Reducing the size of or eliminating these machines would substantially reduce the capital cost required to build paraxylene units as well as reduce energy consumption and operating costs. These processes also require costly heat exchange equipment to perform refrigerant cooling in addition to the high cost of the coolant utilities themselves. Thus, there is a need for a more cost effective mechanism for performing refrigeration in paraxylene recovery processes.

Ammonia Absorption Refrigeration (AAR) can be a cost-effective, energy saving process that has been used for providing moderate temperature refrigeration. In AAR, an enthalpy source such as waste heat reboils an ammonia fractionator that is fed a stream enriched in ammonia relative to water, (also shown as strong aqua in FIG. 6). The fractionator separates the stream enriched in ammonia relative to water into a higher purity ammonia vapor overhead stream, and a stream enriched in water relative to ammonia (also shown as weak aqua in FIG. 6) bottoms stream. The ammonia vapor overhead stream is condensed via air or water cooling to liquid ammonia refrigerant. The liquid ammonia refrigerant is then directed to the refrigerant users. As enthalpy is transferred indirectly from the material being refrigerated, the liquid ammonia refrigerant evaporates and generates ammonia refrigerant vapor. The ammonia vapor is directed to an absorber, along with the stream enriched in water relative to ammonia which absorbs the ammonia vapor while releasing heat of absorption. The heat of absorption is typically removed by water cooling the absorber.

U.S. Pat. No. 4,116,652 issued to Zondek discloses a process for freeze concentration of liquid mixtures including solutions by directly contacting the mixtures with a miscible refrigerant in at least two stages. Zondek discloses that good results are obtained when the product being concentrated is xylene and the refrigerant is ammonia. The process also permits the selected separation of crystals at two or more temperatures where crystals can be removed from a first stage and also from a second stage or succeeding stages.

U.S. Pat. No. 4,331,826 issued to Kagawa discloses a process comprising (1) mixing a paraxylene containing feed with an inert liquid refrigerant, (2) feeding the mixed liquid into a lower part of a bubble tower type crystallization tower, (3) evaporating the refrigerant to form a slurry of p-xylene crystals in the paraxylene feed, (4) separating the inert refrigerant as a vapor from the liquid surface of an upper part of the crystallization tower, and (5) separating paraxylene crystals from the slurry discharged from the upper part of the crystallization tower. Examples of inert refrigerant include carbon dioxide, ammonia, and lower hydrocarbons having 2 to 4 carbon atoms.

Both the '652 and '826 patents disclose direct contact crystallization processes in which the refrigerant is injected directly into the solution being crystallized. Direct contact cooling with a refrigerant requires costly capital equipment and expenditures in energy to efficiently separate the refrigerant from the hydrocarbon streams being cooled. For this reason, direct contact cooling has found limited commercial applications.

In the context of other pure product or byproduct directed processes, the product must be stripped substantially free of all residual ammonia. In the context of paraxylene recovery, the ammonia refrigerant would need to be reduced to on the order of 1 ppmw from the crystallization section reject filtrate, since it is a severe poison to the acid catalysts used in paraxylene unit isomerization sections.

As a result of these and other challenges, AAR has not been successfully applied for the separation of paraxylene from mixed aromatics.

It has now been found that indirect AAR, in accordance with the present invention, can be utilized to provide cooling for paraxylene crystallization while overcoming the problems realized from processes where ammonia was added directly to the feedstocks.

It has also been found that refrigeration derived from an AAR process comprising certain vaporization, water/ammonia contacting, separating and revaporizing steps in accordance with the present invention, results in substantially improved process economics for paraxylene crystallization than traditional processes relying on capital and energy intensive propane vapor recompression refrigeration systems.

It has also been found that several enthalpy sources distinct to a paraxylene crystallization process can power the integrated AAR in accordance with the present invention, resulting in a substantial savings in energy costs and reduction of undesirable emissions of carbon dioxide to the atmosphere.

SUMMARY OF THE INVENTION

One aspect of this invention is a crystallization process for recovering paraxylene from a substantially hydrocarbon feedstock. The recovery comprises cooling the hydrocarbon feedstock in at least one refrigerated crystallization stage that is indirectly refrigerated by evaporating at least a portion of a substantially liquid stream comprising ammonia.

Another aspect of this invention is a crystallization process for recovering paraxylene from a substantially hydrocarbon feedstock. The recovery comprises cooling the hydrocarbon feedstock in at least one refrigerated crystallization stage that is cooled by an ethylene refrigerant. The ethylene refrigerant is cooled by heat exchange with a substantially liquid stream comprising ammonia.

Another aspect of this invention is a crystallization process for recovering paraxylene from a substantially hydrocarbon feedstock. The recovery comprises cooling the hydrocarbon feedstock in at least one refrigerated crystallization stage that is refrigerated by a series of cooling substeps. These substeps comprise contacting a stream comprising ammonia vapor with water and forming a mixture comprising water and ammonia, and further recovering a substantially liquid stream comprising ammonia from the mixture comprising water and ammonia. At least a portion of the substantially liquid stream comprising ammonia is vaporized by transferring at least a portion of the enthalpy of vaporization to cooling the hydrocarbon feedstock.

Another aspect of this invention is an ammonia absorption refrigeration process comprising at least one enthalpy source from various locations. These locations include: condensing overhead vapors of distillation towers used to separate products, byproducts, and/or recycle streams of a crystallization process to recover paraxylene; reactor effluent streams of a crystallization process to recover paraxylene; furnace flue gas from a crystallization process to recover paraxylene; steam generated during a crystallization process to recover paraxylene; and other chemical or refinery process units located near a paraxylene crystallization process unit.

The process of the present invention results in substantial benefits over alternative paraxylene recovery processes.

One benefit is that utilizing AAR for paraxylene recovery in accordance with the present invention allows for the elimination of a propane or propylene refrigeration loop commonly used in conventional paraxylene recovery processes. This eliminates the expensive $C_3$ compressor, condenser, flash drums, and other equipment associated with the circuit, as well as elimination of the capitalized utilities associated with running the $C_3$ compressor. The cost of suitable AAR in accordance with the present invention is substantially lower than even the most cost effective and efficient propane vapor recompression systems.

Another benefit is that utilizing AAR for paraxylene recovery in accordance with the present invention consumes waste heat enthalpy from the paraxylene recovery process for reboiling the ammonia fractionator. Waste heat is essentially a free enthalpy source, since it is otherwise lost to the environment via air or water cooling.

Another benefit is that the AAR system is driven by pumps for conveying liquids as compared to refrigeration compressors for conveying gas. Refrigeration compressors are far more costly and require more energy to operate than pumps that convey liquid. Since compression often results in an elevation in the temperature of the compressed gas due to compressor inefficiency, inevitably, additionally cooling utilities are required and energy lost.

Yet another benefit is that utilizing AAR for paraxylene recovery in accordance with the present invention also reduces greenhouse gas emissions. The use of waste heat powered AAR in paraxylene processes generally results in a substantial reduction in electricity consumption from the overall replacement of vapor recompression refrigeration compressors with AAR pumps. Reducing electricity consumption generally leads to lower $CO_2$ emissions, since incremental electricity most often derives from fossil fuel fired power plants or plant furnaces.

DETAILED DESCRIPTION OF THE INVENTION

Figure 1:
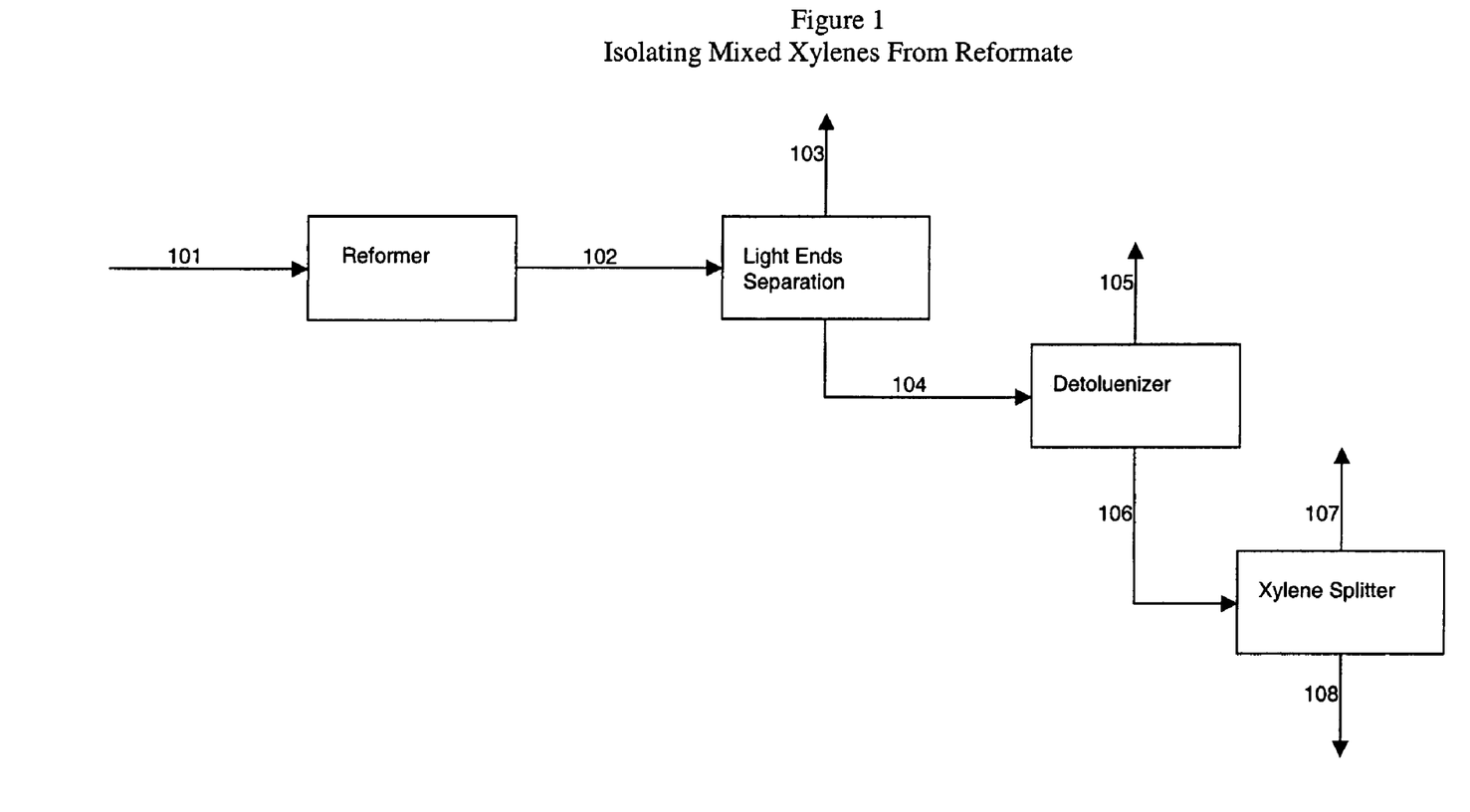
FIG. 1 is a diagram that shows a process for isolating mixed xylenes from a substantially hydrocarbon feedstock processed through a reformer.

Substantially hydrocarbon feedstocks are often generated through a series of processing steps. FIG. 1 is a block diagram for isolating mixed xylenes from a substantially hydrocarbon feedstock processed through a catalytic reformer. Stream 101, is lean in aromatics but high in paraffins and naphthenes, and is sent to the reformer. The reformer cyclizes the paraffins to naphthenes and dehydrogenates the naphthenes to form aromatics. The effluent from the reformer is condensed as effluent stream 102. Stream 102 is fed to one or more distillation towers for removal of lighter hydrocarbon components in an overhead stream, depicted as the Light Ends Separation block. For example, stream 102 may be fed to a debutanizer tower to remove $C_4-$ hydrocarbons overhead as stream 103. The heavier hydrocarbon components in the bottoms, stream 104, contain primarily $C_5+$ hydrocarbons. Alternatively, the Light Ends Separation block may contain several distillation towers that remove light hydrocarbon streams, and isolate a distillation cut enriched in benzene that is then fed to an extraction unit to recover chemical grade benzene. Stream 104 is fed to a Detoluenizer, which is designed for separation of toluene and any $C_7-$ hydrocarbons remaining in stream 104 into stream 105. The bottoms from the Detoluenizer, stream 106, contains $C_8+$ components and is fed to a Xylene Splitter. The Xylene Splitter separates reformate mixed xylenes overhead as stream 107 (also shown as stream 201 in FIG. 2), and a $C_9+$ aromatics bottoms as stream 108.

Figure 2:
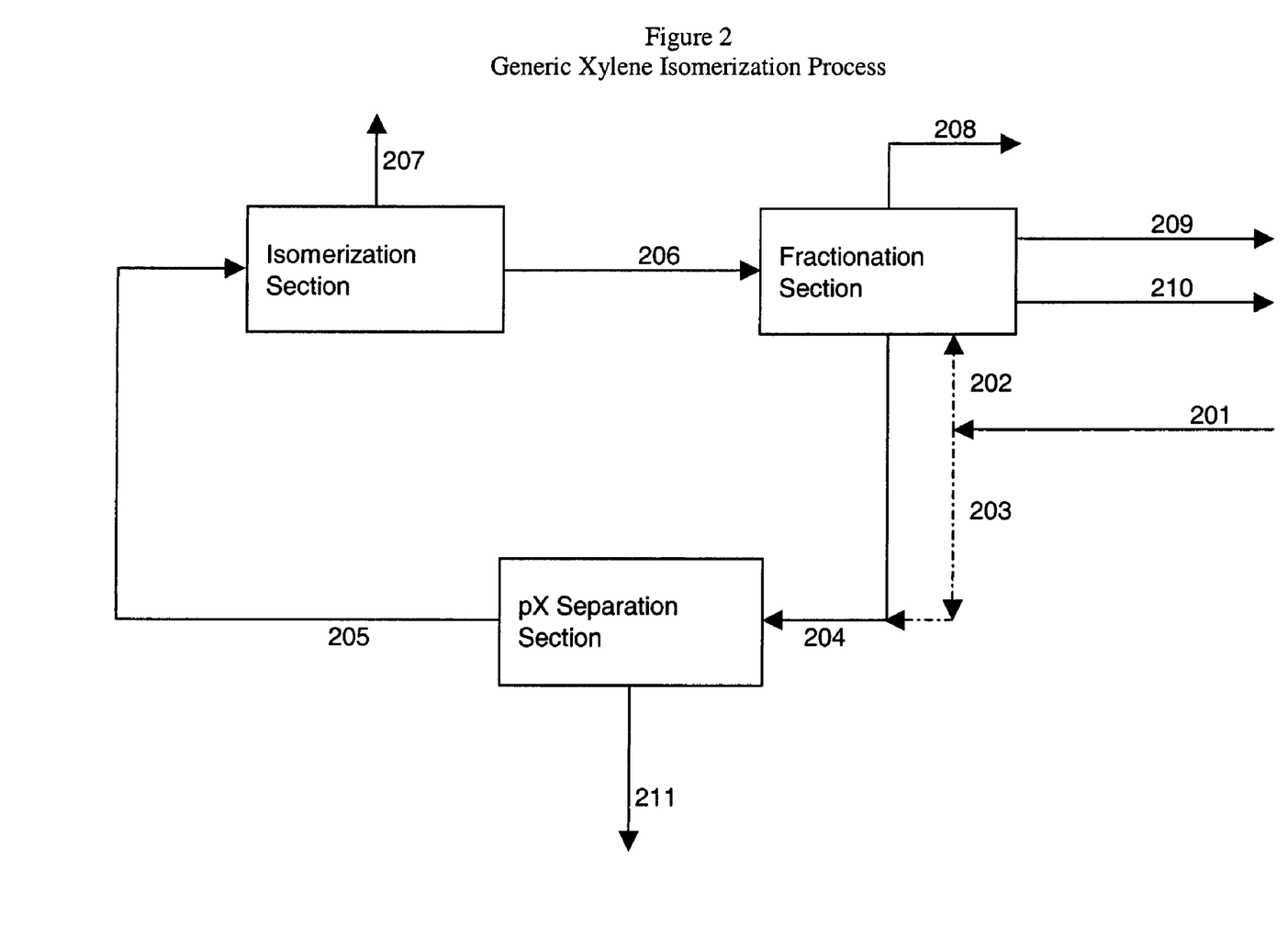
FIG. 2 is a diagram of a xylene isomerization process.

Once the substantially hydrocarbon feedstock derived from reformate is produced, a series of further separations isolates the paraxylene isomer. FIG. 2 is a block diagram of a xylene isomerization process. The reformate feedstock, stream 201, is either fed to the Fractionation Section (to dehydrate it for example) as stream 202 or to the Paraxylene Separation Section as stream 203. Stream 201 generally contains about 10 weight percent to about 20 weight percent ethylbenzene, about 70 weight percent to about 87 weight percent xylene isomers (paraxylene, metaxylene, and orthoxylene) present at a near equilibrium distribution, and a minor amount of other aromatic and non-aromatic hydrocarbon impurities. In this context, equilibrium distribution refers to about 25 percent paraxylene, about 50 percent metaxylene, and about 25 percent orthoxylene. The Fractionation Section provides substantial separation of $C_7-$ and $C_9+$ hydrocarbons produced in the Isomerization Section from the $C_8$ aromatics. Since these are the same functions provided by the Detoluenizer and Xylene Splitter of FIG. 1, one set of towers may be used to process both feedstock unit stream 104 or 106 of FIG. 1 and stream 206 of FIG. 2.

The Fractionation Section in accordance with FIG. 2 produces four streams: 1) off-gas, stream 208; 2) light aromatics, stream 209; 3) heavy aromatics, stream 210; and a $C_8$ aromatics heart cut, stream 204. Off-gas stream 208 contains primarily hydrogen (if the isomerization reactions take place in the presence of hydrogen, as is typical in the majority of commercial paraxylene units), and light hydrocarbons such as ethane, propane, butane, pentane, benzene, etc. produced by ethylbenzene dealkylation and/or the cracking of non-aromatics present in the feed.

Stream 204 contains primarily $C_8$ aromatics, but may also contain minor amounts of light byproducts such as benzene and toluene and minor amounts of heavy aromatics such as $C_9+$ aromatics. Paraxylene cannot be separated economically from the other xylene isomers by distillation due to the close proximity of their respective boiling points. Thus, a portion of the paraxylene in stream 204 (also shown as stream 301 in FIG. 3) is removed in the Paraxylene Separation Section by crystallization processes or selective adsorption processes.

Where the paraxylene is separated by crystallization, the crystallization section generally includes crystallizers, scraped wall heat exchangers, or reslurry drums, either individually or in combination. The Paraxylene Separation section produces two streams: paraxylene product, stream 211, and a paraxylene lean stream, stream 205. Stream 211 is also depicted as stream 336 in FIG. 3 and stream 205 is also depicted as stream 312 of FIG. 3.

After removal of a substantial portion of the paraxylene, Stream 205 is directed to the Isomerization Section, which catalytically reestablishes the xylene isomer equilibrium of about 25 percent paraxylene, about 50 percent metaxylene, and about 25 percent orthoxylene. The Isomerization Section also converts ethylbenzene to byproducts that are lighter or heavier than the $C_8$ aromatics that are distilled in the fractionation section. Side reactions also occur, including xylene disproportionation that converts two moles of xylenes to one mole of toluene and one mole of trimethylbenzenes.

In general, the ethylbenzene conversion and side reactions lead to the formation of byproducts with boiling points lighter than the $C_8$ aromatics, and byproducts with boiling points higher than the $C_8$ aromatics. Light paraffin byproducts such as ethane and propane are removed from the process in Isomerization Section vent gas, stream 207, and Fractionation Section off-gas, stream 208. The primary light aromatic byproducts include benzene and toluene, which are removed in the fractionation section as stream 209. The primary heavy byproducts are primarily $C_9$ and $C_{10}$ aromatics that are removed in stream 210.

Ethylbenzene conversion in the Isomerization Section is typically from about 20 percent to about 80 percent. Due to incomplete ethylbenzene conversion and the equilibrium limitation on the isomerization of the xylene isomers, a substantial recycle loop is established between the sections. The paraxylene concentration in stream 204 is typically only about 19 to about 23 weight percent paraxylene when processing reformate mixed xylenes feedstock.

Separation of xylene isomers by crystallization is more commercially viable than separation by fractionation because the xylene isomers all boil in close proximity to each other. Paraxylene has the highest melting point of the $C_8$ aromatic isomers (paraxylene has a melting point of about 55.9° F., metaxylene has a melting point of about −54.2° F., and orthoxylene has a melting point of about −13.4° F.) and is the first isomer to crystallize as the temperature of the crystallization section feed is reduced. Eventually, a sufficiently low temperature is reached where another xylene isomer begins to co-crystallize. This is usually metaxylene for stream compositions normally found in paraxylene processes, but can be orthoxylene depending on the composition. For reformate mixed xylenes, the temperature at which metaxylene begins to co-crystallize is known as the paraxylene-metaxylene eutectic temperature and occurs at about −90° F. Even at this low temperature, paraxylene has appreciable solubility in the liquid phase of about 7.3 mole percent. It is desirable to recover paraxylene at a temperature within a few degrees of the eutectic temperature to reduce paraxylene solubility and thus reduce recycle throughout the process. It is generally not desirable to crystallize below the eutectic temperature since co-crystallization of other isomers occurs, which leads to increased recycle or problems with downstream equipment.

Figure 3:
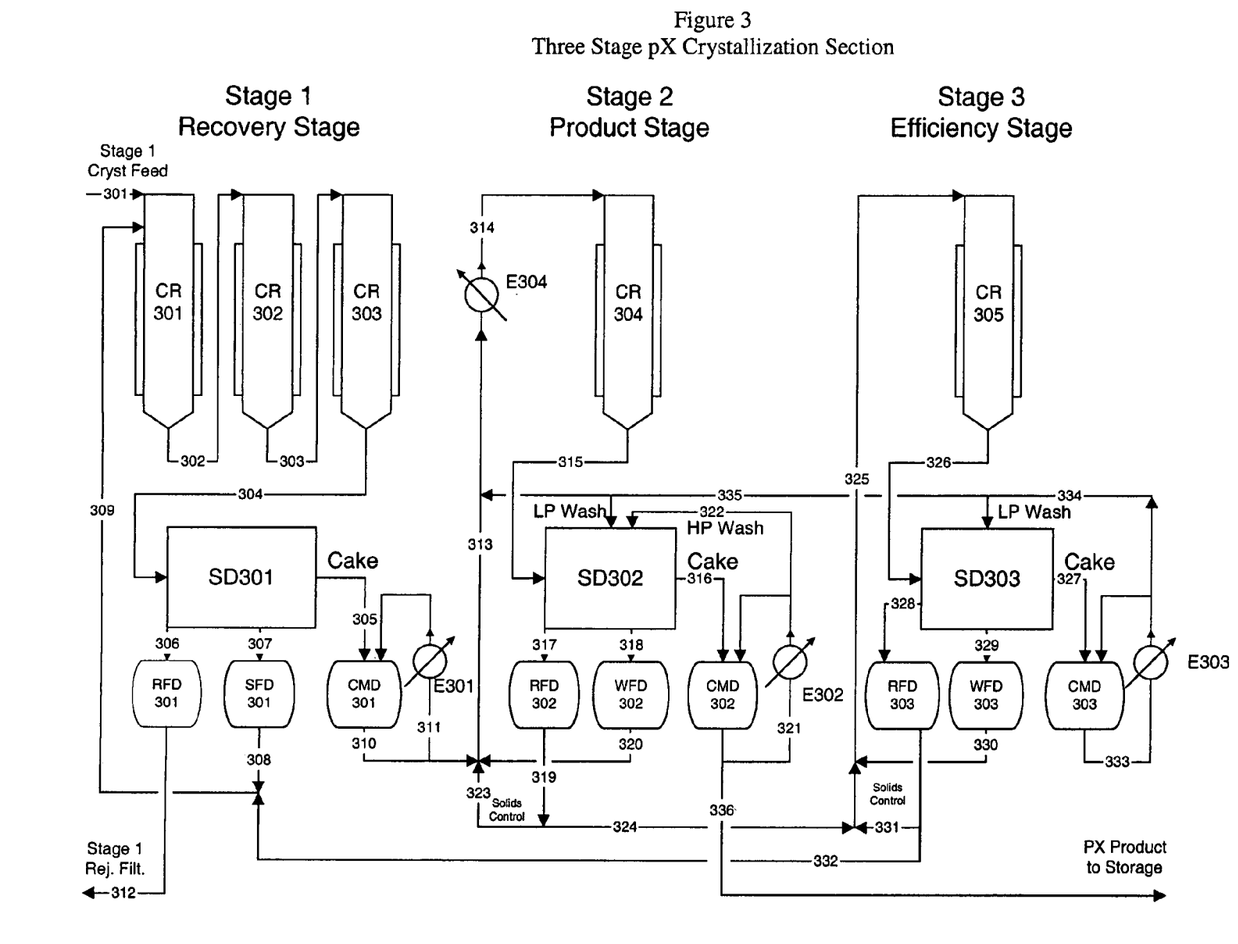
FIG. 3 is a diagram of a conventional paraxylene crystallization process.

FIG. 3 is a detailed sketch of a 3-stage paraxylene crystallization section comprising a first (recovery) stage, a second (product) stage and a third (efficiency) stage. The crystallization section produces two streams: 1) a final, high purity paraxylene product, stream 336, and 2) reject filtrate, stream 312. Stream 312 of FIG. 3 is stream 205 of FIG. 2. Stream 312 ranges from about 7 to about 12 weight percent paraxylene, and stream 336 is typically at least about 99 weight percent paraxylene, more typically at least about 99.7 weight percent paraxylene. Stream 312 is recycled back to the Isomerization Section of FIG. 2, where the ortho and metaxylene-rich isomers are isomerized to near equilibrium, and ethylbenzene is converted to light and heavy byproducts. These byproducts can be readily separated from the $C_8$ aromatics by distillation in the Fractionation Section of FIG. 2.

In FIG. 3, crystallization section feed, stream 301, is directed to the first (recovery) stage and has a paraxylene content of about 15 to about 25 weight percent, more typically 19 to 23 weight percent. Stream 301 is cooled by heat exchange with stream 312 to within a few degrees of the temperature at which paraxylene crystals begin to form. This step is not shown in FIG. 3. This step may involve an optional trim cooler.

When paraxylene is removed from the feed, the effluent has less mass than the original crystallization feed, and thus, may not be able to supply sufficient cooling to reach the desired temperature. In the present invention, boiling liquid ammonia refrigerant from the AAR may be utilized to provide incremental cooling to the optional trim cooler, in addition to cooling provided by stream 312.

Stream 301 is directed to a first (recovery) stage where it is cooled to within a few degrees of the eutectic temperature by passage through a series of refrigerant cooled crystallizers, CR 301, CR 302, and CR 303. Examples of suitable refrigerants include, but are not limited to ammonia, ammonia/water mixtures, ethylene, ethane, and carbon dioxide. The preferred refrigerant is ethylene.

The contents of CR 301 are typically cooled to about −45° F. to about −65° F. using high pressure (about 80 psia to about 122 psia) ethylene refrigerant. This provides an ethylene evaporation temperature about 25° F. lower than the contents of the crystallizer. A temperature difference between the refrigerant and crystallizer contents is required to affect the indirect heat transfer of the present invention. Indirect heat transfer means that the refrigerant is not in direct contact with the material being cooled, but rather, the refrigerant and the material being cooled are on opposite sides of a heat transfer surface. For this present invention, the refrigerant is a substantially liquid stream comprising ammonia and the material being cooled is the substantially hydrocarbon feedstock. CR 301 effluent, stream 302, is conveyed to crystallizer CR 302. The contents of CR 302 are cooled to about −65° F. to about −80° F. using medium pressure (about 59 psia to about 91 psia) ethylene refrigerant. The effluent from CR 302, stream 303, is conveyed to crystallizer CR 303, where it is cooled by low pressure (about 42 psia to about 58 psia) ethylene refrigerant to within a few degrees of the paraxylene-metaxylene eutectic temperature, typically to about −80° F. to about −93° F. Effluent from CR 303, stream 304, is conveyed to a solid/liquid separation device, SD 301. The temperature of the stream 304 arising from CR 303 is typically about −80° F. to about −95° F.

SD 301 may be a centrifuge (preferably a screen bowl centrifuge), a filter (such as a rotary vacuum filter), or some other solid-liquid separation device. SD 301 separates stream 304 into streams 306 and 307, and paraxylene wet cake 305. Stream 306 is collected in reject filtrate drum, RFD 301, and recycled back to the Isomerization Section of FIG. 2. If SD 301 is a screen bowl centrifuge, a paraxylene enriched, screen filtrate stream, stream 307, may optionally be isolated and sent to screen filtrate drum, SFD 301, and then recycled back to crystallizer CR 301 via streams 308 and 309. Streams 308 and 309 typically have a paraxylene content higher than stream 301, and thus, are recycled back to CR 301.

Wet paraxylene cake 305 is also produced from SD 301. This cake has a high concentration of the other $C_8$ aromatics. Thus, cake 305 is not pure enough to be final paraxylene product. Cake 305 generally comprises at least 70 weight percent paraxylene and preferably, at least about 80 weight percent paraxylene. Cake 305, is directed to cake melt drum, CMD 301, where it is melted by circulating the cake melt through melt heater, E 301, and back to CMD 301. Heat is typically supplied to E 301 via a warm paraxylene unit stream or via steam. Stream 311 is removed as a slip stream from the outlet (Stream 310) of cake melt drum CMD 301 and is circulated through E 301 as explained above. CMD 301 is typically on level control that is cascaded to a flow controller that directs the other part of stream 310 to the second or successive crystallization stage. This part of stream 310 is combined with solids control stream, stream 323.

In the second (product) or successive crystallization stage, paraxylene product is withdrawn. Due to the higher paraxylene concentration of cake 305, paraxylene recovery can be achieved by crystallizing at a temperature close to the melting point of pure paraxylene. The second (product) stage crystallizer, CR 304, typically operates at about 35° F. to about 44° F. In the processes of this invention, mixtures comprising ammonia and/or ammonia and water are preferred for providing the 10 cooling for CR 304 and the optional E 304, as will be discussed below.

The effluent from CR 304, stream 315, is conveyed to a solid/liquid separation device, SD 302. SD 302 is preferably a pusher-type centrifuge. SD 302 separates stream 315 into at least two streams, including a wet paraxylene cake 316, and stream 317. Stream 317 is collected in reject filtrate drum RFD 302. Cake 316 is directed to cake melt drum CMD 302 via stream 321, where it is melted by circulating cake melt through melt heater E 302 and back to CMD 302. Where cake 316 is washed, a wash filtrate stream, stream 318, is isolated and sent to wash filtrate drum, WFD 302, via stream 318, and recycled back to CR 304 via streams 313, 314, and 320. The reject filtrate, stream 319, is lean in paraxylene relative to stream 314, but often high in paraxylene relative to stream 301 or stream 312. Part of stream 319 is recycled to CR 304 via stream 323 to control the solids content in CR 304 at a desired level, which is typically in the range of about 35 to about 50 weight percent solids. The other part of stream 319 is sent to a third or successive crystallization stage via stream 324.

The third (efficiency) stage crystallizer CR 305 operates at a lower temperature than the second stage crystallizer CR 304. CR 305 typically operates in the range of about −10° F. to about 20° F. The purpose of this third stage is to crystallize and recover paraxylene from the second stage reject filtrate, stream 324, and to minimize recycle back to the second stage. This improves the efficiency of the overall crystallization process.

The effluent from CR 305, stream 326, is pumped to a solid/liquid separation device, SD 303. SD 303 is preferably a pusher-type centrifuge. SD 303 separates stream 326 into at least two streams, including cake 327 and stream 328. Cake 327 is directed to cake melt drum CMD 303 through stream 333, where it is melted by circulating cake melt through melt heater E303 and back to CMD 303. Stream 328 is collected in reject filtrate drum, RFD 303. If SD 303 is a pusher centrifuge, optionally a separate wash filtrate stream, stream 329, is isolated and sent to wash filtrate drum, WFD 303, and recycled back to CR 305 via streams 325 and 330. A portion of the stream arising from RFD 303, stream 331, is recycled back to CR 305 to control the solids content in CR 305 within the range of about 30 weight percent to about 50 weight percent solids. The balance of the stream arising from RFD 303 is recycled back to CR 301 via stream 332.

In FIG. 3, cake 316 and cake 327, are melted through melt heaters E 302 and E 303, respectively. Part of the circulating melt arising from CMD 302 leaves as paraxylene product, stream 336. Stream 336 is generally at least about 99 weight percent paraxylene and typically at least about 99.7 weight percent paraxylene. The other part is fed back to SD 302 to be used as high purity cake wash stream 322 (depicted as HP wash in FIG. 3). Part of the third stage cake melt arising from CMD 303 is optionally used as low purity cake wash (depicted as LP wash in FIG. 3) in SD 303 and/or SD 302, and part is recycled to the second stage crystallizer CR 304 via streams 334 and 335.

In an alternate embodiment of the 3-stage crystallization section to recover paraxylene from a substantially hydrocarbon feedstock derived from reformate, cake 305 is directed to a reslurry drum, which replaces crystallizer CR 304 of FIG. 3. This is done in lieu of directing stream 305 to melt drum CMD 301. Stream 305 is not melted. Stream 305 is slurried in solids control recycle, stream 323, and optionally heated via exchanger E 304 to control temperature in the slurry drum to about −10° F. to about 20° F.

Also, rather than directing cake 316 into melt drum CMD 302, cake 316 is directed into a second slurry drum which replaces CR 305. Thus, melt drum CMD 302 and exchanger E 302 do not exist. Cake 316 is slurried in solids control recycle stream, stream 325, to achieve a solids concentration in the reslurry drum of about 30 weight percent to about 50 weight percent solids. In addition, the temperature in the second slurry drum is controlled to about 30° F. to about 45° F., preferably to about 37° F. to about 42° F. by optionally adding heat exchange into stream 325. Cake 327 is melted and a portion is taken as final, high purity (at least about 99.7 weight percent paraxylene) product, and a portion is used as high purity cake wash for the cake in SD 303.

Since cakes 305 and 316, respectively, are not melted before directing them to the reslurry drums, there is no need to remove heat via refrigeration from the reslurry drums. In the processes of this invention, the refrigeration duty used in the first stage of the crystallization section is preferably ethylene refrigeration used to cool crystallizers CR 301, CR 302, and CR 303, and AAR preferably provides refrigeration duty used in a trim cooler in the crystallization section feed/effluent heat exchanger train and to condense ethylene used to cool the first stage crystallizers.

While any one of a number of refrigerants, including, but not limited to, ethane, ethylene, propane, propylene, ammonia and ammonia/water mixtures may be used, an ethylene refrigeration loop is preferred source for cooling the first stage crystallizers.

Figure 4:
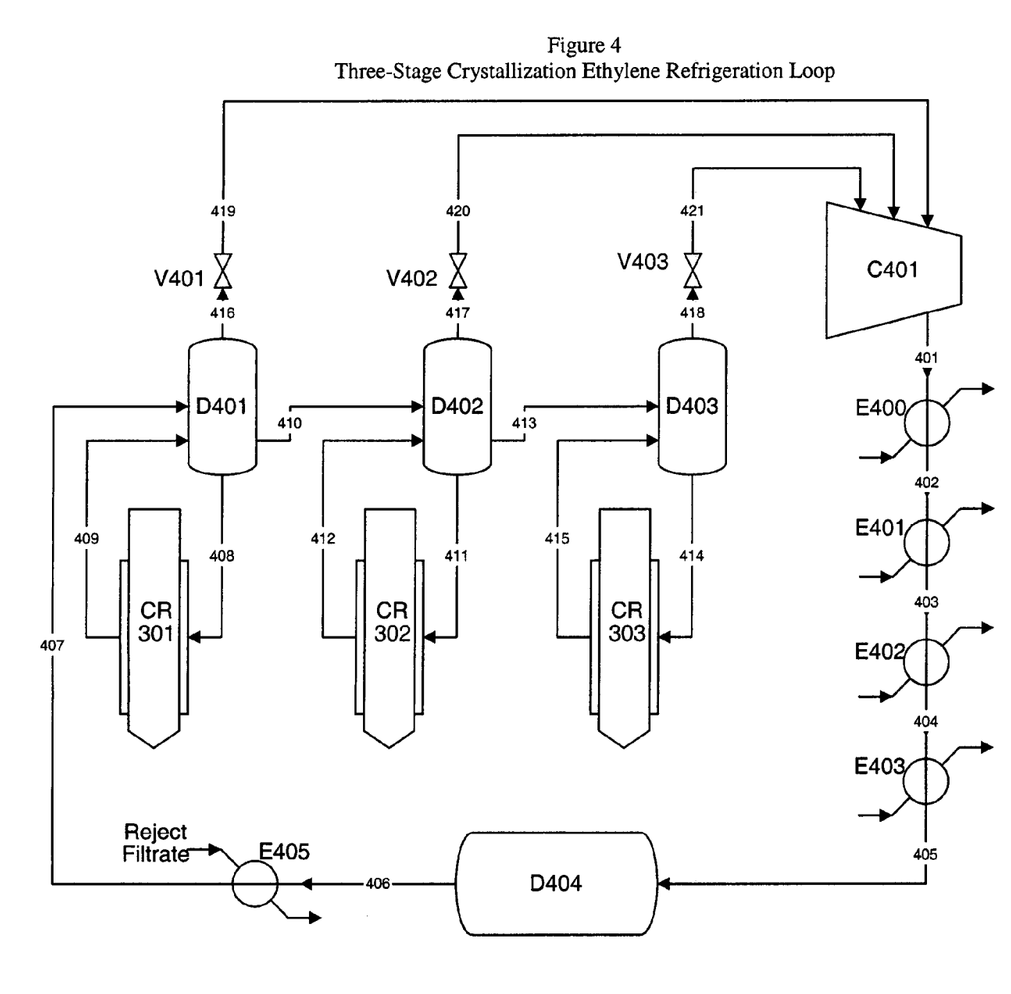
FIG. 4 is a diagram of an ethylene refrigeration loop used in a paraxylene recovery process.

FIG. 4 is a depiction of an ethylene refrigeration loop for the 3-stage crystallization process of FIG. 3. In FIG. 4, compressed ethylene gas, streams 401, 402, 403, and 404 are optionally desuperheated by passage through one or more optional exchangers, E 400, E 401, and/or E 402 The compressed ethylene gas is condensed in exchanger E 403.

Condensed ethylene, stream 405, is pressured to the ethylene accumulator D 404. Stream 406 is optionally subcooled in E 405 with stream 312 of FIG. 3, and then sent to a low pressure ethylene head drum D 401 as stream 407. D 401 is typically elevated above CR 301. Liquid ethylene from D 401 circulates through the jacket of CR 301 via thermosyphon action through streams 408 and 409.

The pressure of D 401 is controlled via pressure control valve V 401 to maintain the circulating ethylene at a temperature about 20° F. to about 35° F. colder than the contents within CR 301 to provide an adequate rate of heat transfer. Vapor leaving D 401 is sent to a low pressure stage of ethylene compressor C 401 via streams 416 and 419. As heat is transferred from the CR 301 contents to the ethylene, it at least partially vaporizes. The vapor generated by heat transfer is sent to a compressor C 401 as noted above.

Low pressure (about 42 to about 58 psia) ethylene is pressured from D 401 to the medium pressure ethylene head drum, D 402, via stream 410. Liquid ethylene from D 402 circulates through the jacket of CR 302 via thermosyphon action through streams 411 and 412. The pressure of D 402 is controlled via pressure control valve V 402. Vapor leaving D 402 is sent to a medium pressure stage of ethylene compressor C 401 via streams 417 and 420. The pressure of D 402 is controlled to provide a temperature of the ethylene circulating through streams 411 and 412 that is about 20° F. to about 35° F. lower than the contents of CR 302.

Medium pressure (about 59 to about 91 psia) ethylene is pressured from D 402 to a high pressure ethylene head drum D 403 via stream 413. High pressure (about 80 to about 122 psia) ethylene circulates through the jacket of CR 303 via thermosyphon action through streams 414 and 415. The pressure of D 403 is controlled via pressure control valve V 403 to provide an ethylene temperature of stream 415 that is about 20° F. to about 35° F. lower than the contents of CR 303. The vapor from D 403 is directed to the suction of compressor of C 401 via streams 418 and 421.

The ethylene vapor exiting the crystallizer jackets above is compressed to a pressure high enough to enable it to be condensed at a reasonable temperature. Ethylene compressor outlet pressure is typically in the range of about 250 psig to about 350 psig and more typically about 275 psia to about 310 psia. It is generally not practical to compress the ethylene to a pressure at which it can be condensed in an air or water cooled exchanger, because the critical temperature of ethylene (about 49° F.) is typically below the temperature of ambient air or the available cooling water at most locations.

In the present invention, ethylene is condensed and optionally desuperheated by exchange with ammonia refrigerant. The ammonia evaporation temperature in the ammonia condenser is typically in the range of about −10° F. to about −50° F. In the processes of this invention, liquid ammonia refrigerant can also be used to provide refrigeration or cooling of one or more of or all three stages of a three stage crystallization process. Preferably, the liquid ammonia refrigerant is used in one or preferably both of the second and/or third stage crystallizers. Ammonia is vaporized by heat indirectly transferred from the second and third stage crystallizers in which it is used. Indirect heat transfer means that the refrigerant is not in direct contact with the material being cooled, but rather, the refrigerant and the material being cooled are on opposite sides of a heat transfer surface. Liquid ethylene refrigerant is vaporized by heat transfer from the first stage crystallizer and the ethylene vapor would be compressed and condensed and optionally desuperheated by vaporization of ammonia liquid.

Another substantially hydrocarbon feedstock for producing paraxylene is a mixed xylene stream formed in a selective toluene disproportionation (STDP) section. Such a stream generally contains greater than about 70 weight percent paraxylene in the stream. In a typical STDP section, fresh toluene feed and, optionally, recycled toluene feed is directed to an STDP Reactor. The STDP reactor represents an entire vapor phase reactor section including a reactor, furnace, preheat exchangers and reactor effluent coolers, separator drum, recycle gas compressor, etc. required to carry out the STDP reactions over a catalyst in the vapor phase in the presence of hydrogen rich recycle gas.

The STDP reactor produces a condensed reactor effluent which contains benzene and a $C_8$ fraction with high paraxylene concentration as well as unreacted toluene and light and heavy byproducts. This effluent is sent to a stabilizer to produce a stabilizer off-gas, which contains mainly hydrogen dissolved in the condensed reactor effluent and light hydrocarbons produced by cracking reactions occurring over the catalyst. The stabilizer also generates a bottom stream, which is sent to a detoluenizer.

The detoluenizer produces a $C_7-$ overhead stream, containing mainly benzene co-product and unreacted toluene plus a minor amount of light hydrocarbon byproducts not removed in the stabilizer and a $C_8+$ bottoms stream. The detoluenizer overhead is fed to a benzene tower, which produces: 1) a high purity benzene co-product as a sidedraw; 2) a benzene drag stream that contains a small portion of the benzene and light hydrocarbons from the detoluenizer overhead; and 3) recycle toluene feed that is subsequently directed to the STDP reactor. The detoluenizer bottoms is fed to a xylene tower which produces: 1) a high paraxylene concentration stream, that typically contains at least about 70 weight percent paraxylene, and preferably at least about 80 weight percent paraxylene, which is subsequently directed to a paraxylene crystallization section; and 2) a heavy aromatics stream, comprising $C_9+$ aromatics. The paraxylene crystallization section produces a final, high purity paraxylene stream, containing at least about 99.7 weight percent paraxylene.

Figure 5:
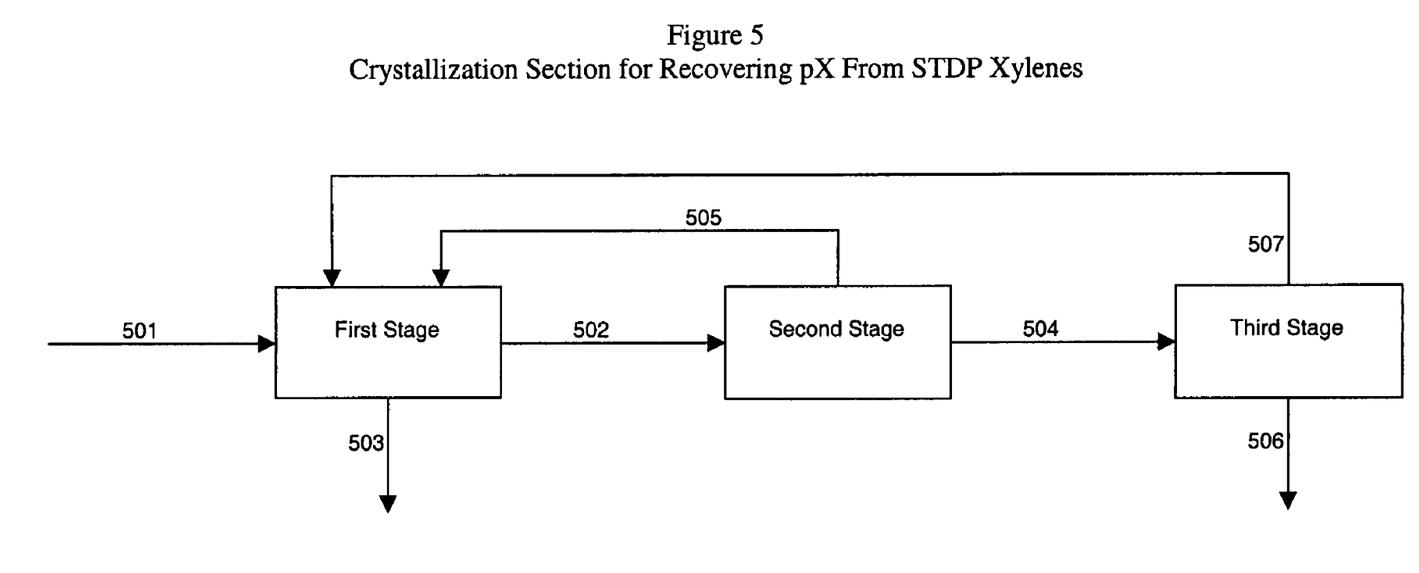
FIG. 5 is a diagram for a paraxylene crystallization process for recovering paraxylene from Selective Toluene Disproportionation (STDP).

A block diagram of a paraxylene crystallization section for a substantially hydrocarbon feedstock with high paraxylene concentration, an STDP xylenes feedstock, is provided in FIG. 5. This particular configuration of the crystallization section is comprised of three stages, with each stage comprised of crystallizers operating at a particular stage temperature, paraxylene solids separation devices such as filters or centrifuges, etc., similar to the stages of the crystallization section of a paraxylene process that recovers paraxylene from reformate xylenes shown in FIG. 3.

For the embodiment for processing STDP xylenes, the cake from each stage is melted and the paraxylene product is withdrawn from the first stage. The second and third stages have scavenger functions which increase the overall paraxylene recovery of the process. Stream 501, which has a paraxylene weight percent preferably of at least 70 weight percent, is fed to the first stage, which typically operates at a temperature of about 35° F. to about 43° F. and more typically at a temperature of about 37° F. to about 42° F.

For the present invention, heat is removed from the stages of the crystallization section. This can be performed through indirect heat transfer with an ammonia refrigerant. The first stage produces two streams: high purity paraxylene product, stream 503, and first stage reject filtrate, stream 502. Stream 502 is fed to the second stage, which is a scavenger stage that typically operates at about −10° F. to about 20° F. The second stage produces two streams: second stage cake melt, stream 505, and second stage reject filtrate, stream 504. Stream 505 has a high paraxylene concentration, but not high enough to be final, paraxylene product. Thus, stream 505 is recycled to the first stage. Stream 504, is fed to the third stage. The third stage produces two streams: third stage cake melt, stream 507, which is recycled back to the first stage, and third stage reject filtrate or reject xylenes, stream 506.

The paraxylene concentration in the reject filtrate of a particular stage is determined primarily by the stage temperature, and to a minor extent, by the efficiency of the paraxylene solids separation device. If the process were operated with only the first stage, paraxylene recovery would be low. This is because much of the paraxylene would be lost via stream 502 due to the high solubility of paraxylene in stream 502, based on the high temperature at which the first stage operate would need to operate. This can often justify the capital and energy cost associated with adding another stage (here, the second stage) with a scavenger function. Similarly, the relatively high solubility of paraxylene in stream 504, and consequently its high volume can also often justify adding another stage (here, the third stage), depending on the concentration of impurities (compounds other than paraxylene) in stream 501.

Were the paraxylene concentration in stream 501 sufficiently low, perhaps as low as about 50 percent, about 60 percent or even about 70 weight percent, it may be desirable to operate the third stage crystallizers at a sufficiently low temperature (about −30° F. to about −50° F.) to require ethylene refrigeration.

For the present invention, ammonia may be vaporized by enthalpy transferred indirectly from the first and second stage crystallizers. For purposes of the present invention, indirect heat transfer means that the refrigerant is not in direct contact with the material being cooled, but rather, the refrigerant and the material being cooled are on opposing sides of a heat transfer surface. Liquid ethylene refrigerant is generally vaporized by heat transfer from the third stage crystallizer, and, for the present invention, condensed and optionally desuperheated by vaporization of ammonia liquid.

Ammonia evaporation temperatures as low as about −50° F. can readily be achieved in an AAR system comprising an ammonia refrigerant. This is sufficient to condense ethylene at typical ethylene compressor discharge pressures, to provide cooling duty to help crystallize paraxylene in the first, but preferably the second and third stages of FIG. 3 and the first and second stages of FIG. 5, and to service all other coolers within the process, to the extent such services could have feasibly been cooled by a $C_3$ refrigerant. For example, at a pressure of about 321.4 psia, ethylene condenses at a temperature of about −13° F., and at a pressure of about 243.6 psig, ethylene condenses at a temperature of about −31° F.

Figure 6:
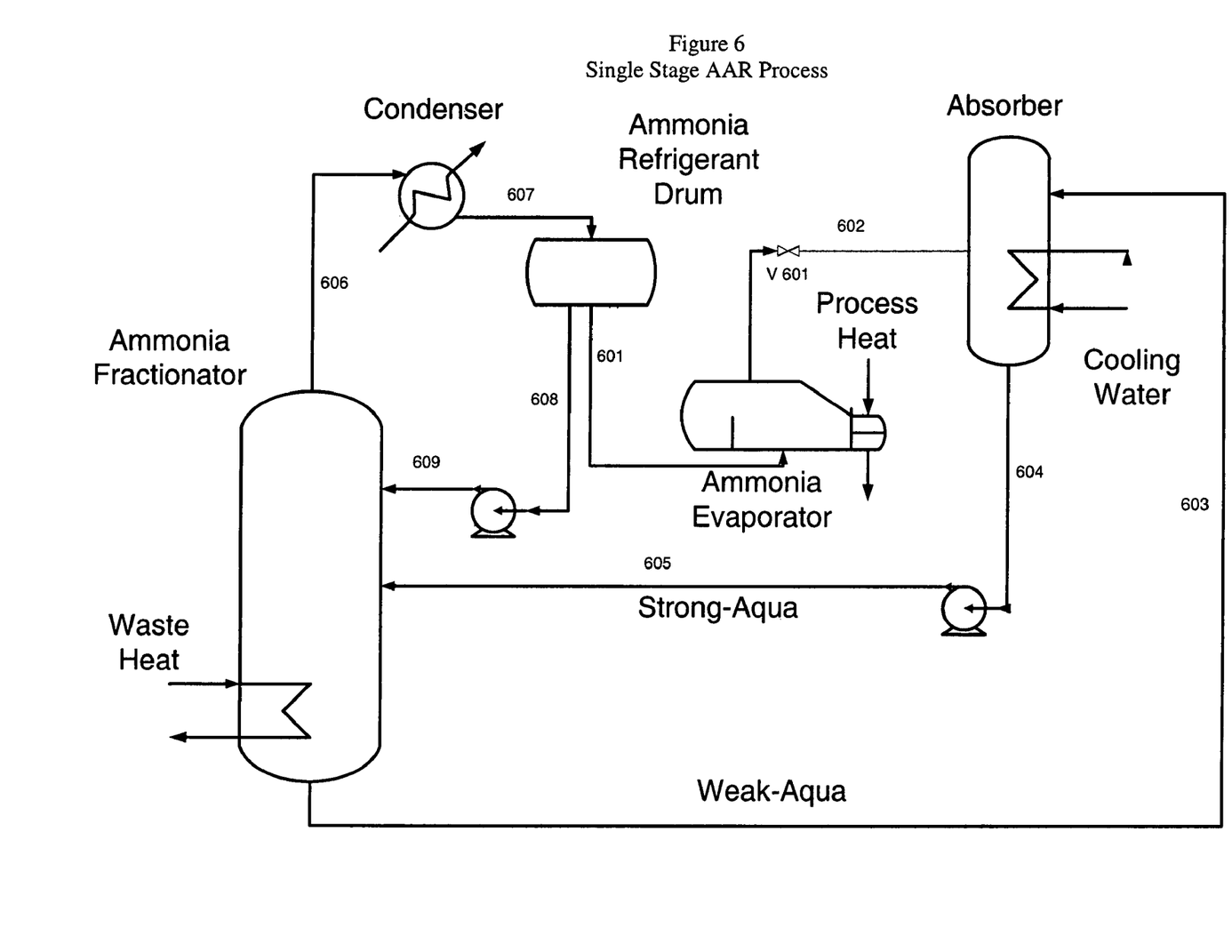
FIG. 6 is a diagram of an ammonia absorption refrigeration process.

A single-effect AAR cycle is shown in FIG. 6. Liquid ammonia, stream 601, is conveyed to the Ammonia Evaporator. For the processes described in this invention, the Ammonia Evaporators are chillers that remove process heat. Process heat from the paraxylene crystallization process is transferred to the ammonia refrigerant which causes the ammonia to vaporize.

A pressure control valve V 601 used on stream 602 is used to control pressure on the ammonia side of the Ammonia Evaporator. At lower pressure, ammonia boils at a lower temperature. A temperature difference is required between the ammonia and the process side fluid in the evaporator to provide heat transfer. In ammonia cooled heat exchangers, this temperature difference is typically in the range of about 4° F. to about 15° F. In crystallizers, this temperature difference is typically about 15° F. to about 40° F., more typically about 20° F. to about 30° F. Thus, the pressure of the Ammonia Evaporator, is controlled by the pressure control valve V 601 Ammonia vapor, stream 602, is sent to an Absorber, where it is contacted with a weak ammonia aqua solution (enriched in water relative to ammonia), stream 603. The absorption of ammonia into water is exothermic. Thus, cooling water is used to cool the Absorber to drive the absorption. The Absorber generates a strong ammonia aqua solution (enriched in ammonia relative to water), stream 604, that is pumped to an Ammonia Fractionator as stream 605.

A waste heat enthalpy source may be and is preferably used to reboil the Ammonia Fractionator. Very pure ammonia vapor (typically at least about 99 weight percent) is taken overhead in the Ammonia Fractionator. The Ammonia Fractionator overhead vapor, stream 606, is generally condensed against air or more typically against cooling water. At least a portion of this condensed ammonia is commonly vaporized by indirect transfer of heat from the hydrocarbon feedstock to said condensed ammonia. Indirect heat transfer means that the refrigerant is not in direct contact with the material being cooled, but rather, the refrigerant and the material being cooled are on opposite sides of a heat transfer surface. The condensed ammonia is directed to an Ammonia Refrigerant Drum via stream 607. A pump is used to send reflux from the reflux drum to the Ammonia Fractionator as shown in streams 608 and 609.

Advanced AAR cycles, including multi-stage absorption refrigeration systems, multiple-lift refrigeration cycles, advanced absorption vapor exchange GAX cycles, and multiple effect absorption cycles, as described in U.S. Pat. No. 5,097,676, U.S. Pat. No. 5,966,948, Erickson and Tang, "Evaluation of Double-Lift Cycles for Waste Heat Powered Refrigeration," Intl. Absorption Conf., Montreal, Canada, Sept. 17-22 (1996), Erickson, Potnis, and Tang, "Triple Effect Absorption Cycles," Proc. Intersoc. Energy Convers. Eng. Conf. (1996), $31^{st}$, 1072-1077, Rane and Erickson, "Advanced absorption cycle: vapor exchange GAX," Am. Soc. Mech. Eng. (1994) 25-32, and Richter, "Multi-Stage Absorption Refrigeration Systems," Journal of Refrigeration, September/October 1962, are hereby incorporated by reference. The use of advanced AAR cycles to provide refrigeration to condense ethylene and crystallize paraxylene can also be used for this invention because these cycles use less heat and lower temperature heat sources than simpler AAR cycles, and they can accommodate refrigeration at multiple temperature levels and heat sources at multiple temperature levels. Advanced AAR cycles can have multiple absorbers and multiple ammonia fractionators.

In FIG. 4, E 403, and optional E 400, E 401, E 402 ethylene desuperheaters may also concurrently serve as ammonia evaporators for purposes of the present invention. Thus, AAR condenses and optionally desuperheats the ethylene vapor generated during the crystallization of paraxylene from low paraxylene concentration streams. When AAR is used to crystallize paraxylene from high paraxylene concentration streams in a jacketed scraped wall crystallizer, the jacket is an Ammonia Evaporator of FIG. 6.

It is generally most preferred to completely forego or replace the propane or propylene refrigeration circuit with an AAR circuit, since this allows complete elimination of the energy intensive $C_3$ compressor, condenser, flash drums, and other equipment associated with the circuit, as well as elimination of the utilities consumption associated with running the $C_3$ compressor. The evaporators are generally the interface between the refrigeration circuit and the process. The mixed xylenes stream being cooled is on the hot side of the evaporator, and evaporating refrigerant is on the cold side of the evaporator. Thus, when retrofitting AAR to replace a C3 refrigeration circuit, the evaporators may remain in place and boiling ammonia refrigerant replaces boiling $C_3$ refrigerant on cold side of the evaporator.

Retrofitting a paraxylene recovery unit having a $C_3$ refrigeration circuit with an AAR system will generally result in lower electricity consumption and higher waste heat utilization. The major power input to conventional $C_3$ refrigeration cycles is in the form of electricity or steam used to power the compressor motor. The major power to an AAR unit is the waste heat enthalpy source used to reboil the ammonia fractionator. Waste heat is essentially free energy, since it is otherwise lost to the environment via air or water cooling. Thus, replacing the $C_3$ refrigeration cycle with an AAR refrigeration cycle generally leads to savings of at least the electricity or steam required to power the drivers of the propane or propylene compressors of conventional paraxylene units, since only a small amount of electricity or steam is required to power the drivers of the pumps associated with the AAR.

For purposes of the present invention it is preferable that at least portion of the waste heat enthalpy source used in the AAR fractionator is derived from a heat source available on the paraxylene unit, from a unit that produces feed for the paraxylene unit, or from a unit that is located near the paraxylene unit. Suitable sources of heat to the AAR ammonia fractionator are those that are available at a supply temperature of at least 200° F., and preferably at least 250° F. for best results. Higher enthalpy source stream temperatures are preferred since they generally lead to higher AAR process efficiency.

One suitable enthalpy source on the paraxylene unit is hot isomerization reactor effluent. Using this stream as the heat source also serves the purpose of cooling this stream to allow separation of condensable hydrocarbons from the recycle gas, which is required before this gas is sent back to the recycle gas compressor suction.

Another suitable enthalpy source is the condensing overhead vapors of any fractionation section stabilizers or xylene splitter columns present at a paraxylene or related operating facilities. Using these streams as the heat source serves the purpose of performing required condensation of these streams while reducing cooling utility requirements.

Still another suitable enthalpy source may be the process streams that must be cooled before moving to the next unit operation within the paraxylene process. Using these streams as the AAR enthalpy source also serves the purpose of cooling these streams before sending them to the next unit operation within the paraxylene process.

Other suitable enthalpy sources on the paraxylene unit include the flue gas of the isomerization section furnace or the flue gas of the fractionation section reboilers where these reboilers are fired heaters.

Suitable enthalpy sources for the AAR units of this invention include the condensing overhead vapors or hot product streams from detoluenizer and xylene splitter fractionator towers found in hydrocarbon feedstock preparation process steps. As shown in FIG. 1, a feedstock preparation unit that isolates paraxylene unit mixed xylenes feed from reformate generally includes at least two fractionation towers. One tower, the detoluenizer, separates lighter boiling compounds such as benzene, toluene, and light non-aromatics from the close boiling $C_8$ aromatics, and another tower, the Xylene Splitter block, separates the $C_8$ aromatics from the higher boiling $C_9$ and heavier aromatics and higher boiling non-aromatics. Suitable enthalpy sources for the AAR units of this invention include the condensing overhead vapors or hot product streams from these towers. Using these streams as the heat source also serves the purpose of cooling these streams, which reduces the size of the equipment needed to cool these streams to their target temperatures, and in some cases eliminates the need for extra equipment and reduces the consumption of cooling utilities.

Enthalpy sources for the AAR are not limited to those described. They can also include heat sources available on other nearby chemical or refinery process units, and steam which may be available from these units or site utilities units. The use of a waste heat enthalpy source from paraxylene process streams, heat from processes that produce a feed stream to the paraxylene unit, or heat sources available on other chemical or refinery process units located near the paraxylene unit provides synergy between the paraxylene process and these other processes.

The process of the present invention results in substantial benefits over alternative paraxylene recovery processes. One benefit is that utilizing AAR for paraxylene recovery in accordance with the present invention allows for the elimination of a propane or propylene refrigeration loop commonly used in conventional paraxylene recovery processes. This eliminates the expensive $C_3$ compressor, condenser, flash drums, and other equipment associated with the circuit, as well as elimination of the capitalized utilities associated with running the $C_3$ compressor. The cost of suitable AAR in accordance with the present invention is substantially lower than even the most cost effective and efficient propane vapor recompression systems.

Another benefit is that utilizing AAR for paraxylene recovery is that replacing the $C_3$ refrigeration cycle will lead to energy savings approximately equal to the electricity or steam required to power the drivers of the propane or propylene compressors of conventional paraxylene units, since only a small amount of electricity or steam is required to power the drivers of the pumps associated with AAR.

Another benefit is that utilizing AAR for paraxylene recovery in accordance with the present invention consumes waste heat enthalpy from the paraxylene recovery process for reboiling the ammonia fractionator. Waste heat is essentially a free enthalpy source, since it is otherwise lost to the environment via air or water cooling.

Another benefit is that the AAR system is driven by pumps for conveying liquids as compared to refrigeration compressors for conveying gas. Refrigeration compressors are far more costly and require more energy to operate than pumps that convey liquid. Since compression often results in an elevation in the temperature of the compressed gas due to compressor inefficiency, inevitably, additionally cooling utilities are required and energy lost.

Another benefit is that utilizing AAR for paraxylene recovery in accordance with the present invention also reduces greenhouse gas emissions. The use of waste heat powered AAR in paraxylene processes generally results in a substantial reduction in electricity consumption from the overall replacement of vapor recompression refrigeration compressors with AAR pumps. Reducing electricity consumption generally leads to lower $CO_2$ emissions, since incremental electricity most often derives from fossil fuel fired power plants or plant furnaces.

EXAMPLE 1

Example 1 illustrates how waste heat available on a xylene isomerization unit that uses reformate mixed xylenes feedstock, and waste heat from the towers of a unit for isolating mixed xylenes feedstock from reformate can be used to power an AAR unit in a cascaded ethylene/AAR refrigeration section of a xylene isomerization unit.

This first part of Example 1 describes using propylene refrigeration to provide cooling duty for comparison purposes to describe the eventual benefits provided by the process steps of the present invention Heating and cooling duties for the xylene isomerization unit and the towers for recovering mixed xylenes from reformate in this example were obtained from computer simulation. For this example, the crystallization section is of the alternate embodiment of the three-stage crystallization section of FIG. 3, comprised of ethylene cooled scraped wall crystallizers in a first stage, and two reslurry scavenger stages. No refrigeration duty is required by the second and third reslurry stages. The unit produces 110,647 lb/hr of paraxylene from reformate derived mixed xylenes.

The first stage crystallizers operate at three step temperatures of −63° F., −80.5° F., and −90° F. The crystallization section feed is first cooled to −39° F. by exchange with first stage reject filtrate and a propylene cooled trim cooler. In a conventional xylene isomerization unit design, the ethylene vapors generated in the first stage crystallizer jackets is compressed and desuperheated and then condensed by liquid propylene refrigerant. Propylene refrigeration is also used on a miscellaneous user, which is a condenser that recovers condensibles from the off-gas of the fractionation section stabilizer. The propylene refrigeration duties and corresponding propylene evaporation temperatures are listed below:

|  | Duty (MMBTU/hr) | Propylene Evaporation Temperature (° F.) |
| --- | --- | --- |
| Stabilizer Knock-back condenser | 0.50 | 40.0 |
| Crystallization feed trim cooler | 4.15 | 10.8 |
| Ethylene desuperheater | 5.18 | 5.4 |
| Ethylene Condenser | 24.79 | −35.0 |
| Total | 34.62 | |

363,354 lb/hr of reformate which has been first treated in a light ends separation section to remove benzene and lighter hydrocarbons to produce a stream containing 0.6 weight percent benzene is then processed in two towers (a detoluenizer and a xylene splitter) to isolate 148,950 lb/hr reformate mixed xylenes feedstock. The detoluenizer and xylene splitter are heat integrated in that the condensing overhead vapors of the xylene splitter are used to reboil the detoluenizer, and the xylene splitter is operated at sufficient pressure to provide an approximately 20° F. delta T for the detoluenizer reboiler. The detoluenizer tower overhead pressure is 31 psia. In a conventional process, the detoluenizer overhead vapor is condensed via an air cooler, and 68.1 MMBTU/hr is removed in the detoluenizer condenser in condensing and cooling the detoluenizer overhead vapor from 274.2° F. to 256.5° F.

The fractionation section of the xylene isomerization unit consists of a single tower that separates a light aromatic stream overhead, a heavy aromatics bottoms stream, and a $C_8$ heart cut as a sidedraw. After using this stream to preheat the isomerization section liquid feed, and then splitting off small streams to provide heat for miscellaneous uses within the xylene isomerization unit, in a conventional process the stream is cooled from 281.8° F. to 111° F. via a water cooler that removes 57.5 MMBTU/hr heat before the stream is sent to the crystallization section. This stream could supply 30.1 MMBTU/hr to an AAR unit in cooling it from 281° F. to 196.5° F.

In the xylene isomerization process described in this invention, the following heat sources would be available to power an advanced multi-stage AAR:

|  | Duty (MMBTU/hr) |
| --- | --- |
| Detoluenizer overhead vapor | 68.1 |
| Fractionation section sidedraw | 30.1 |
| Total | 98.2 |

The propylene evaporation temperatures of the conventional xylene isomerization unit are within the range that can be achieved by advanced multi-stage AAR units, and the heat source temperatures are sufficient to power the AAR fractionator. The AAR need only achieve a coefficient of performance (refrigeration duty supplied by the AAR divided by the waste heat source duty applied to the AAR) of 0.35 to be powered by the identified heat sources, which is in the range of an advanced multi-stage AAR refrigeration unit in accordance with the present invention. If need be, these heat sources could be supplemented by steam produced in the convection sections of the isomerization furnace and/or the xylene isomerization unit fractionation section reboiler. Thus, it is possible to replace the propylene refrigeration loop with an AAR as described in this invention, with little or no supplemental heat from steam. In so doing, the electricity needed to power the driver of the propylene compressor of the conventional unit would be eliminated, which is approximately 5.0 MW. The size of the air cooled detoluenizer condenser and the sidedraw water cooler would be substantially reduced in size. Synergy is achieved between the xylene isomerization unit and the unit that isolates mixed xylenes from reformate.

EXAMPLE 2

This example will illustrate how waste heat available on an STDP unit can be used to power an AAR unit in a cascaded ethylene/AAR refrigeration section used to supply cooling required by a crystallization unit designed to recover paraxylene from the STDP mixed xylenes.

The first part of this Example 2 describes using propylene refrigeration to provide cooling duty, but this is done for comparison purposes to describe the eventual savings provided by AAR. The STDP unit produces a nominal 92,000 lb/hr of STDP xylenes having a paraxylene content of about 81 weight percent. In a conventional process the first and second stage crystallizers are cooled via propane refrigeration. The third stage crystallizer is cooled via ethylene refrigeration. The propane refrigeration loop is also used to condense the ethylene. Refrigeration duties and propane evaporation temperatures are as listed below:

|  | Duty (MMBTU/hr) | Propane Evaporation Temperature (° F.) |
|---|---|---|
| Stage 1 Crystallizers | 9.8 | 12 |
| Stage 2 Crystallizers | 5.6 | −10 |
| Ethylene Condenser | 4.4 | −35 |
| Total | 19.8 | |

Part of the detoluenizer overhead vapor is used to reboil the benzene tower. However, in a conventional process, there is a supplemental air cooler that condenses the rest. The detoluenizer operates with an overhead pressure of 73.7 psia. In condensing and cooling the detoluenizer overhead vapors from 343.4° F. to 331.3° F., this air cooler removes 50.3 MMBTU/hr. The conventional unit uses a water cooled xylene tower condenser. The xylene tower operates at an overhead pressure of 24.7 psia. In condensing and cooling the xylene tower overhead vapor from 318.8° F. to 302.2° F., the condenser removes 33.6 MMBTU/hr. Thus, in a new STDP/crystallization process described in this invention, these two heat sources are among those available on the STDP unit to power the AAR unit:

|  | Duty (MMBTU/hr) |
|---|---|
| Detoluenizer Overhead Condenser | 50.3 |
| Xylene Tower Overhead Condenser | 33.6 |
| Total | 83.9 |

The propane evaporation temperatures of the conventional STDP unit are within the range that can be achieved by an AAR process in accordance with the present invention, and the heat source temperatures are sufficient to power the AAR. There would be ample waste heat available and at sufficient temperature to power an AAR with a coefficient of performance as low as 0.236. Thus, there is adequate waste heat available from the STDP unit detoluenizer and xylene splitter towers to power the fractionator of an AAR needed to supply the refrigeration duties listed in this example. Thus, it is possible to replace the propane refrigeration loop with an AAR as described in this invention. In so doing, the electricity needed to power the driver of the propylene compressor of the conventional unit would be eliminated, which is approximately 2.7 MW. The size of the air cooled detoluenizer condenser and the xylene tower water cooled condenser would be substantially reduced in size. Synergy is achieved between the STDP section and the crystallization section that recovers paraxylene from the STDP mixed xylenes.

EXAMPLE 3

This example will illustrate a 3-stage crystallization process for recovering paraxylene from reformate mixed xylenes feedstock wherein AAR is used to refrigerate the second and third stage crystallizers and to subcool and condense ethylene which is used to refrigerate the first stage crystallizers.

The first part of Example 3 describes using propylene refrigeration to provide cooling duty, but this is done for comparison purposes to describe the eventual savings provided by AAR. Heating and cooling duties for the xylene isomerization unit and the towers for recovering mixed xylenes from reformate in this example were obtained from computer simulations. For this example, the conventional xylene isomerization crystallization section is of the three-stage design illustrated in FIG. 3 and described above, comprised of ethylene cooled scraped wall crystallizers in a first stage, and propane cooled second and third stage crystallizers. The unit produces 125,351 lb/hr of paraxylene from reformate derived mixed xylenes.

The first stage crystallizers operate at three step temperatures of −54.2° F., −71.9° F., and −82.8° F. The second stage operates at 37.5° F. The third stage operates at 16.6° F. The crystallization section feed is first cooled to −37.8° F. by exchange with first stage reject filtrate and a propane cooled trim cooler. In the conventional xylene isomerization unit design, the ethylene vapors generated in the first stage crystallizer jackets are compressed and desuperheated and then condensed by propane refrigerant. In this example, three desuperheaters are used in series. The compressed ethylene vapors are first desuperheated by exchange with a cool process stream (third stage melt), and then they are further desuperheated in two propane cooled desuperheaters with propane at two different evaporation pressures and thus two different evaporation temperatures, before being condensed by propane at an even lower evaporation temperature and pressure. In this example, propane refrigerant is not used on the knock-back condenser of the fractionation section. The propane compressor of the conventional paraxylene unit requires 7.7 MW of electrical power.

The conventional unit propane refrigeration duties and corresponding propane evaporation temperatures are listed below:

|  | Duty (MMBTU/hr) | Propane Evaporation Temperature (° F.) |
|---|---|---|
| Crystallization feed trim cooler | 3.68 | 1.3 |
| E401 Ethylene desuperheater | 1.06 | 48.5 |
| E402 Ethylene desuperheater | 4.05 | 1.3 |
| Ethylene Condenser | 29.88 | −41.2 |
| Stage 2 Crystallizer | 11.28 | 14.3 |
| Stage 3 Crystallizer | 4.10 | −7.7 |
| Total | 54.05 | |

450,000 lb/hr of reformate which has been first treated in a light ends separation section to remove benzene and lighter hydrocarbons to produce a stream containing 0.6 weight percent benzene is then treated in two towers (a detoluenizer and a xylene splitter) to isolate 184,469 lb/hr reformate mixed xylenes feedstock. The detoluenizer and xylene splitter are heat integrated in that the condensing overhead vapors of the xylene splitter are used to reboil the detoluenizer, and the xylene splitter is operated at sufficient pressure to provide an approximately 20° F. delta T for the detoluenizer reboiler. The detoluenizer tower overhead pressure is 31 psia. In a conventional tower configuration, the detoluenizer overhead vapor is condensed via an air cooler, and 84.3 MMBTU/hr is removed in the detoluenizer condenser in condensing and cooling the detoluenizer overhead vapor from 274.2° F. to 256.5° F. 5.6 MMBTU/hr of 150 psig steam is generated in the convection section of the paraxylene unit isomerization section furnace.

In a xylene isomerization process as described in this invention, the following heat sources are made available to power an advanced multi-stage AAR:

|   | Duty (MMBTU/hr) |
|---|---|
| Detoluenizer overhead vapor | 84.3 |
| Steam generated in the isom furnace | 5.6 |
| Total | 89.9 |

The propylene evaporation temperatures of the conventional xylene isomerization unit are within the range that can be achieved by AAR process steps in accordance with the present invention, and the heat source temperatures are sufficient to power the AAR fractionator. If an advanced multistage AAR unit has a coefficient of performance as low as 0.33, 163.8 MMBTU/hr of heat would be required to generate the 54.05 MMBTU/hr of refrigeration required. The two identified paraxylene unit heat sources could supply about 55% of this need. To allow complete replacement of the conventional propane refrigeration system by an advanced AAR, supplemental steam is imported as needed. To reduce the amount of imported steam, other paraxylene unit warm process streams could be used as AAR waste heat streams.

The process shall be described for the purposes of illustration only in connection with certain embodiments. However, it is recognized that various changes, additions, improvements, and modifications to the illustrated embodiments may be made by those persons skilled in the art, all falling within the scope and spirit of the invention.

That which is claimed is:

1. A crystallization process for recovering paraxylene from a substantially hydrocarbon feedstock comprising cooling said hydrocarbon feedstock in at least one refrigerated crystallization stage that is indirectly refrigerated by evaporating at least a portion of a substantially liquid stream comprising ammonia wherein said at least one crystallization stage is refrigerated by:
    a) evaporating at least a portion of said substantially liquid stream comprising ammonia from enthalpy supplied by a heat source from said crystallization process, and
    b) absorbing said evaporated ammonia from step (a) into a stream comprising a mixture enriched in water relative to ammonia.

2. The process of claim 1 wherein said substantially hydrocarbon feedstock comprises hydrocarbons consisting essentially of ethylbenzene, paraxylene, metaxylene, orthoxylene, and hydrocarbon impurities.

3. The process of claim 1 wherein said substantially hydrocarbon feedstock comprises a low paraxylene concentration of less than about 50 weight percent paraxylene.

4. The process of claim 1 wherein said substantially hydrocarbon feedstock comprises a low paraxylene concentration of less than about 30 weight percent paraxylene.

5. The process of claim 1 wherein said substantially hydrocarbon feedstock comprises a high paraxylene concentration of at least about 50 weight percent paraxylene.

6. The process of claim 1 wherein said substantially hydrocarbon feedstock comprises a high paraxylene concentration of at least about 70 weight percent paraxylene.

7. The process of claim 1 wherein said at least one crystallization stage removes from said hydrocarbon feedstock a stream of at least 70 weight percent paraxylene, further wherein said process produces a final paraxylene product.

8. A crystallization process for recovering paraxylene from a substantially hydrocarbon feedstock comprising cooling said hydrocarbon feedstock in at least one refrigerated crystallization stage that is indirectly refrigerated by cooling substeps comprising:
    a) contacting a stream comprising ammonia vapor with a stream comprising water and forming a liquid mixture comprising water and ammonia,
    b) recovering from said liquid mixture comprising water and ammonia a substantially liquid stream comprising ammonia, and
    c) vaporizing at least a portion of said substantially liquid stream comprising ammonia by transferring at least a portion of the enthalpy of vaporization to said substantially liquid stream comprising ammonia from said hydrocarbon feedstock.

9. The process of claim 8 wherein said liquid mixture comprising water and ammonia of step (a) is further recovered as a stream enriched in ammonia relative to water.

10. The process of claim 9 wherein said stream enriched in ammonia relative to water is directed for fractionation into said substantially liquid stream comprising ammonia and a stream enriched in water relative to ammonia.

11. An ammonia absorption refrigeration process comprising:
    a. conveying a liquid ammonia stream to an ammonia evaporator to chill and remove process heat from a crystallization process to recover paraxylene; b. sending ammonia vapor to an absorber to generate a strong ammonia aqua solution; c. pumping said strong ammonia aqua solution to an ammonia fractionator; d. reboiling said ammonia fractionator with an enthalpy source to create very pure ammonia vapor and then condensing said very pure ammonia vapor, and e. vaporizing at least a portion of said condensed ammonia by indirect heat transfer of heat from a hydrocarbon feedstock to said condensed ammonia, wherein said enthalpy source is selected from the group consisting of: condensing overhead vapors of distillation towers used to separate products, byproducts, and/or recycle streams of a crystallization process to recover paraxylene; reactor effluent streams of a crystallization process to recover paraxylene; furnace flue gas of a crystallization process to recover paraxylene; steam generated during a crystallization process to recover paraxylene; and warm streams on other chemical or refinery process units located near a paraxylene crystallization process unit.

12. The process of claim 11 wherein said enthalpy source is provided at a temperature of at lest about 200° F.

13. The process of claim 11 wherein said enthalpy source is provided at a temperature of at least about 250° F.

* * * * *